United States Patent
Hartley et al.

[11] Patent Number: 5,147,136
[45] Date of Patent: Sep. 15, 1992

[54] TEMPERATURE CYCLING TEST CHAMBERS

[75] Inventors: Jeffrey W. Hartley, Lancaster; Burch E. Zelner, Pataskala, both of Ohio

[73] Assignee: Crane Plastics Company, Columbus, Ohio

[21] Appl. No.: 702,869

[22] Filed: May 20, 1991

[51] Int. Cl.⁵ .................... G01M 19/00; G01N 25/72
[52] U.S. Cl. ...................................... 374/57; 73/865.6
[58] Field of Search ................. 374/57, 45; 73/865.6

[56] References Cited

U.S. PATENT DOCUMENTS

| | | | |
|---|---|---|---|
| 3,488,681 | 1/1970 | Mita et al. | 73/15.4 |
| 3,680,356 | 8/1972 | Felton, Jr. | 374/57 |
| 3,807,216 | 4/1974 | Lindwedel et al. | 73/15 R |
| 4,324,285 | 4/1982 | Henderson | 165/2 |
| 4,575,257 | 3/1986 | Oqura et al. | 374/45 |
| 4,729,246 | 3/1988 | Melgaard et al. | 73/865.6 |
| 4,787,752 | 11/1988 | Fraser et al. | 374/45 |
| 4,807,247 | 2/1989 | Robbins, III | 374/57 |
| 4,854,726 | 8/1989 | Lesley et al. | 374/45 |
| 4,925,089 | 5/1990 | Chaparro et al. | 236/78 |

FOREIGN PATENT DOCUMENTS 1147953  3/1985  U.S.S.R. ................................ 374/57

Primary Examiner—Daniel M. Yasich
Attorney, Agent, or Firm—John L. Gray

[57] ABSTRACT

Two environmental test zones at different temperatures are separated by an insulated wall. A portion of the wall is rotatable and is designed to hold a test specimen thereon. By rotating this portion of the insulated wall, the specimen is exposed to different temperature zones in recurrent cycles. The two temperature zones are readily separable for ease in removing and installing test specimens.

10 Claims, 4 Drawing Sheets

TEMPERATURE CYCLING TEST CHAMBERS

BACKGROUND OF THE INVENTION

At the present time, in order to provide environmental test conditions, full scale test samples are placed in a walk-in size environmental chamber. The chamber is then heated, usually by convection, to an upper air test temperature, typically 180° F., and then held for sample equilibration, typically one-half hour. The chamber is then cooled to a lower test temperature, typically — 20° F. and the chamber air temperature is then again held for typically an hour, to allow sample temperature equilibration. The temperature cycle is then repeated until failure of the test samples is noted by visual inspection. Cycle time is nominally eight hours.

Attempts to speed up this cycle time have been made in the past, as shown in U.S. Pat. No. 2,807,216, Lindwedel, et al., which uses a rotating cylinder containing cavities to hold samples therein and which may be rotated between two test chambers held at different temperatures. Also, U.S. Pat. No. 4,729,246, Melgaard, et al., discloses a plurality of test chambers with products to be tested mounted on a product carrier which in turn is moved by a product carrier transfer assembly.

All of the thermal cycle test systems of the prior art appear to have the disadvantage of either long cycle time or expensive equipment to move a test sample from one temperature zone to another.

SUMMARY OF THE INVENTION

Applicant's invention involves the use of two environmental test zones at different temperatures which are separated by an insulated wall. A portion of the wall is rotatable and of a size so as to hold a test specimen thereon. Simply by rotating this portion of the insulated wall, the specimen is exposed to different temperature zones, each of which is maintained at a selected temperature so that the sample reaches equilibrium very rapidly thus significantly reducing the test time required to evaluate thermal fatigue of test specimens. The device used to accomplish this is simple and low in cost. Using applicant's invention, 40 to 50 cycles per day can be obtained versus three from the prior art since heating and cooling large thermal masses has been eliminated. Dwell time for each thermal cycle is also reduced cutting total cycle time. This is due to actual test samples or replicas temperatures being monitored. This is more efficient than simply monitoring chamber air temperatures and estimating required soak times for sample temperature equilibration.

In one embodiment of the invention, the two temperature zones are readily separable for ease in removing and installing test specimens.

It is therefore an object of this invention to provide a temperature cycling test device which is simple to construct and operate.

It is a further object of this invention to provide a temperature cycling test device which permits a greatly increased number of thermal cycles per day.

It is still another object of this invention to provide such a test chamber wherein the length of time during which the test sample reaches equilibrium is minimized.

These, together with other objects and advantages of the invention will become more readily apparent to those skilled in the art when the following general statements and descriptions are read in the light of the appended drawings.

DETAILED DESCRIPTION OF THE INVENTION

Figure 1:
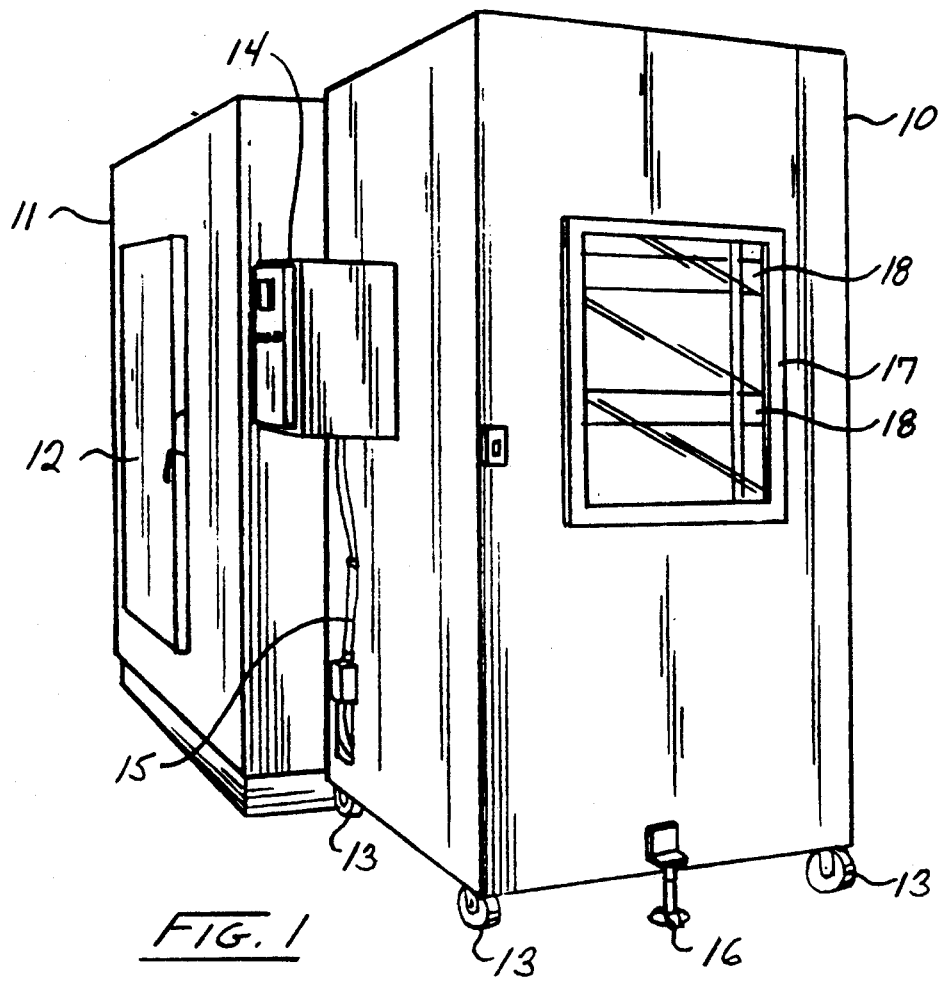
FIG. 1 is a perspective view of the test chambers of the instant invention shown in operating position.

Referring now more particular to FIG. 1, the hot chamber is shown at 10 and the cold chamber is shown at 11. Access to the cold chamber 11 is through door 12 and the hot chamber 10 is mounted on wheels 13—13 so that it may be readily rolled away from the cold chamber 11. Of course, these chambers could be reversed and the stationary chamber could be the hot chamber and the movable chamber could be the cold chamber. Information concerning the temperature conditions in the chamber and of the specimen are displayed in the control cabinet 14 connected to the interior of the chambers by means of electrical connections 15—15. The control cabinet 14, houses the test process controller 42 and the power controller 52 for the heating units 18—18. Stop 16, which when put in place assures that the hot chamber 10 will remain tightly adjacent to the cold chamber 11. Viewing window 17 in the hot chamber 10 may be used to observe specimens under test. The heating units 18—18 which are preferable in the form of quartz tube heating lamps are shown through the window 17.

Figure 2:
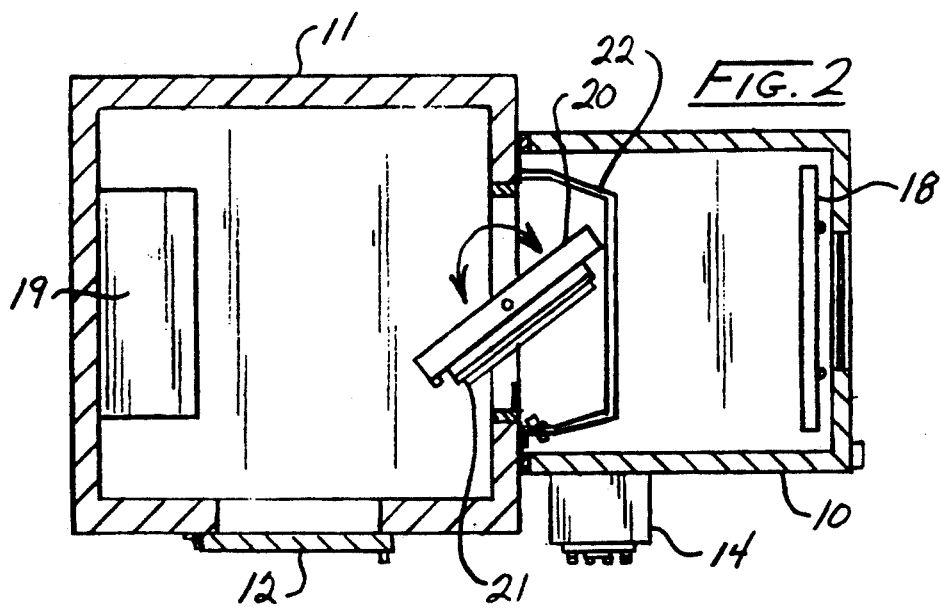
FIG. 2 is a horizontal section through the test chambers of FIG. 1 showing the rotatable portion of the wall.

Referring now more particularly to FIG. 2, the refrigeration unit for cold chamber 11 is shown at 19 and the rotatable wall is shown at 20 in a partially opened position with specimen 21 mounted thereon. Shelf 22 is attached to cold chamber 11 and may be seen more readily in FIG. 3. The rotatable insulated wall portion 20 is shown in closed position with specimen 21 mounted thereon. The wall 20 is rotated by means of motor 23 rotating gear 23a and connected to gear 23b by means of gear belt 24. Sensor 25, which includes relay 21a (See FIG. 7a ), assures that the rotatable wall portion 20 is in fully closed position. Likewise, sensors 78a (including Relay 78) detects wall position 20 degrees before full closing and de-energizes motor 23 and activates hinged stop solenoid valve 79.

Figure 3:
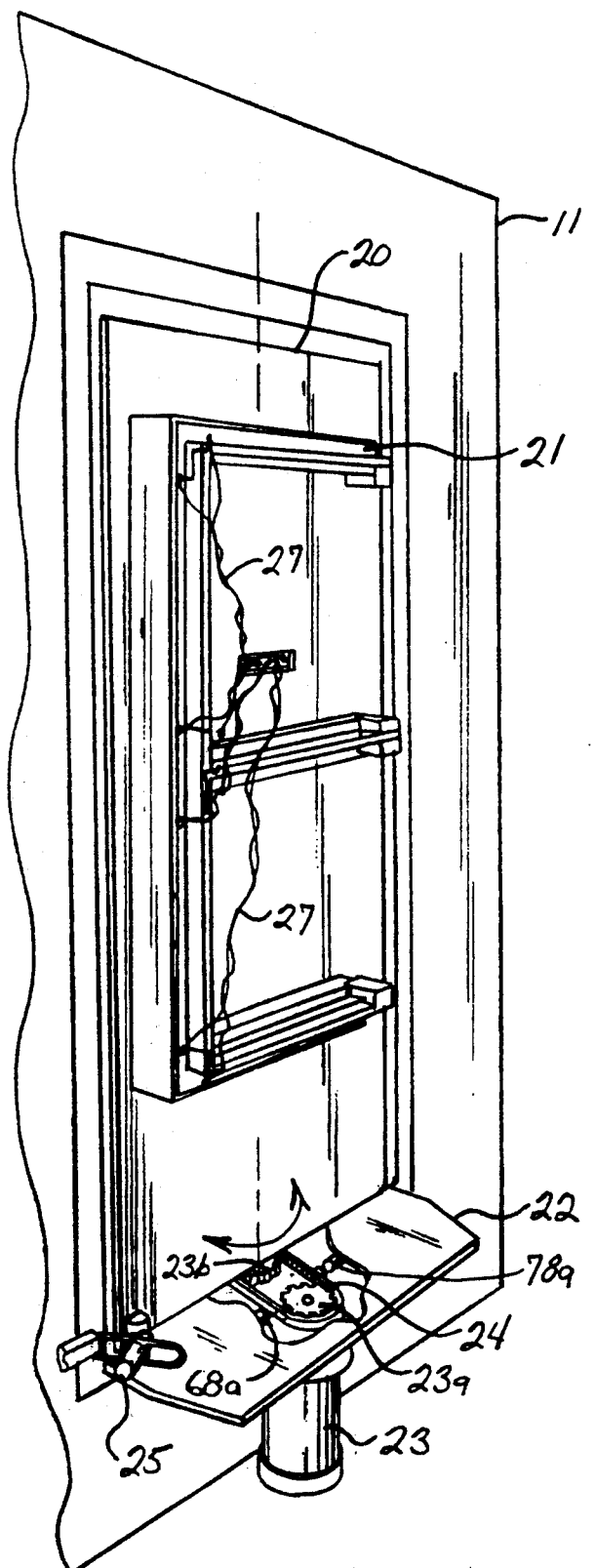
FIG. 3 is a perspective view of a test specimen mounted on the rotatable wall with the hot chamber removed.
Figure 4:
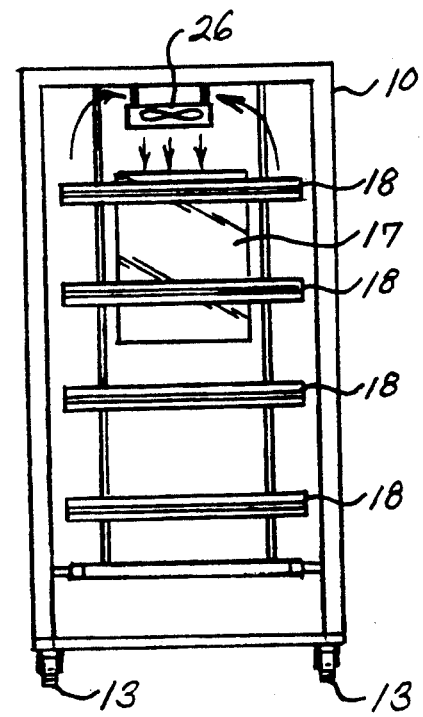
FIG. 4 is an end elevation view of the interior of the hot chamber.
Figure 5:
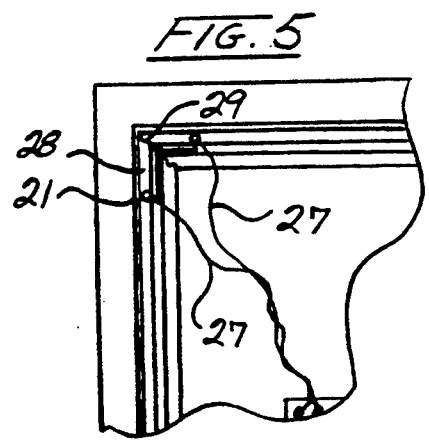
FIG. 5 is a detailed view of the way in which the test specimen is connected to recording data.

Referring now more particularly to FIG. 4, the heat lamps 18—18 are shown as well as a circulating fan 26. The low voltage leads 27—27 shown in FIG. 3 are connected directly to conductive paint on the specimen 21 and are also connected to a standard data recorder (not shown). In the example shown in FIG. 3 the specimen 21 is a portion of a plastic structure. This will be seen more readily in FIG. 5 where the two leads 27—27 are connected to the corner of the plastic structure specimen 21 where fatigue failure cracks are likely to occur. There is conductive paint 28 on this portion of specimen 21 to which the leads 27—27 are connected and as shown, a fatigue crack 29 has occurred thus breaking the circuit.

Figure 6:
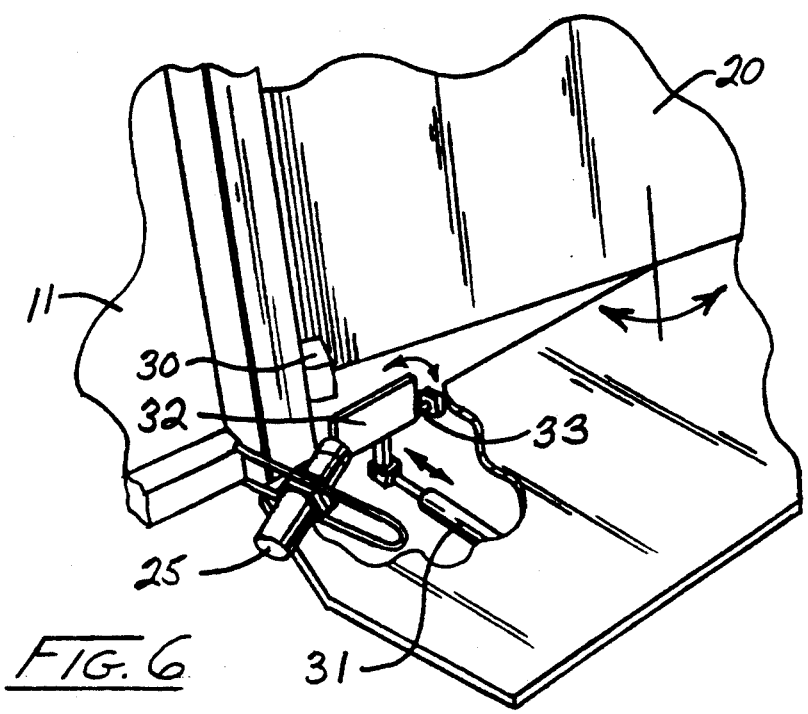
FIG. 6 shows a detailed view of a safety device that assures that the rotatable portion of the wall is in closed position.

Referring now more particularly to FIG. 6, the rotatable insulated wall portion 20 has placed near the bottom thereof and near the edge thereof a target 30 which is observed by sensor 25. This allows power from controller 52 to energize quartz lamps 18—18 for heat cycle portion of the test. Air cylinder 31 is actuated by sensor 68a (FIG. 3), moving hinged stop 32 into position so that the rotatable insulated wall portion 20 will come to the exact closed position. Stop 32 is hinged on shaft 33 so that when the rotatable insulated wall portion 20 moves through its next 180° movement, which is in the reverse direction of its previous movement, the stop 32 will fall down permitting that rotatable insulated wall portion 20 to rotate.

With the test sample 21 secured to the revolving wall section 20, the main power is turned on at 240 volts. The auto manual switch 41 should be set to auto. The controller 42 is programmed in accordance with parameters selected by the operator. The controller 42 is a commercially available unit available from Gulton, West Division, Model 2050. The heat chamber fan switch 43, which controls fan motor 43a which in turn operates fan 26, should be in the on position so as to prevent stratification of heat in the heat chamber side. Motor 43a contains the usual start to run winding changer over contacts 43b. The control power switch 44 is then turned on and the start button 45 on the ramp and soak temperature controller 42 is pushed. The test process controller 42 connects to the thermocouple 42a which is located on the door 20.

Figure 7B:
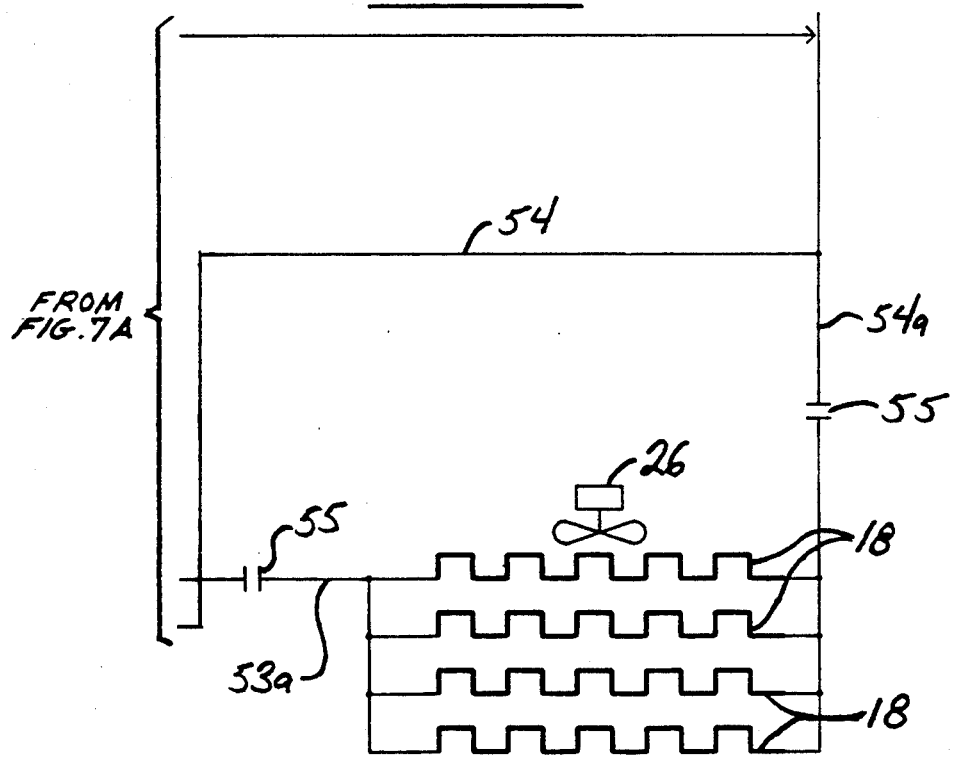
FIG. 7b is a wiring diagram showing the heating elements in the hot chamber.
Figure 7A:
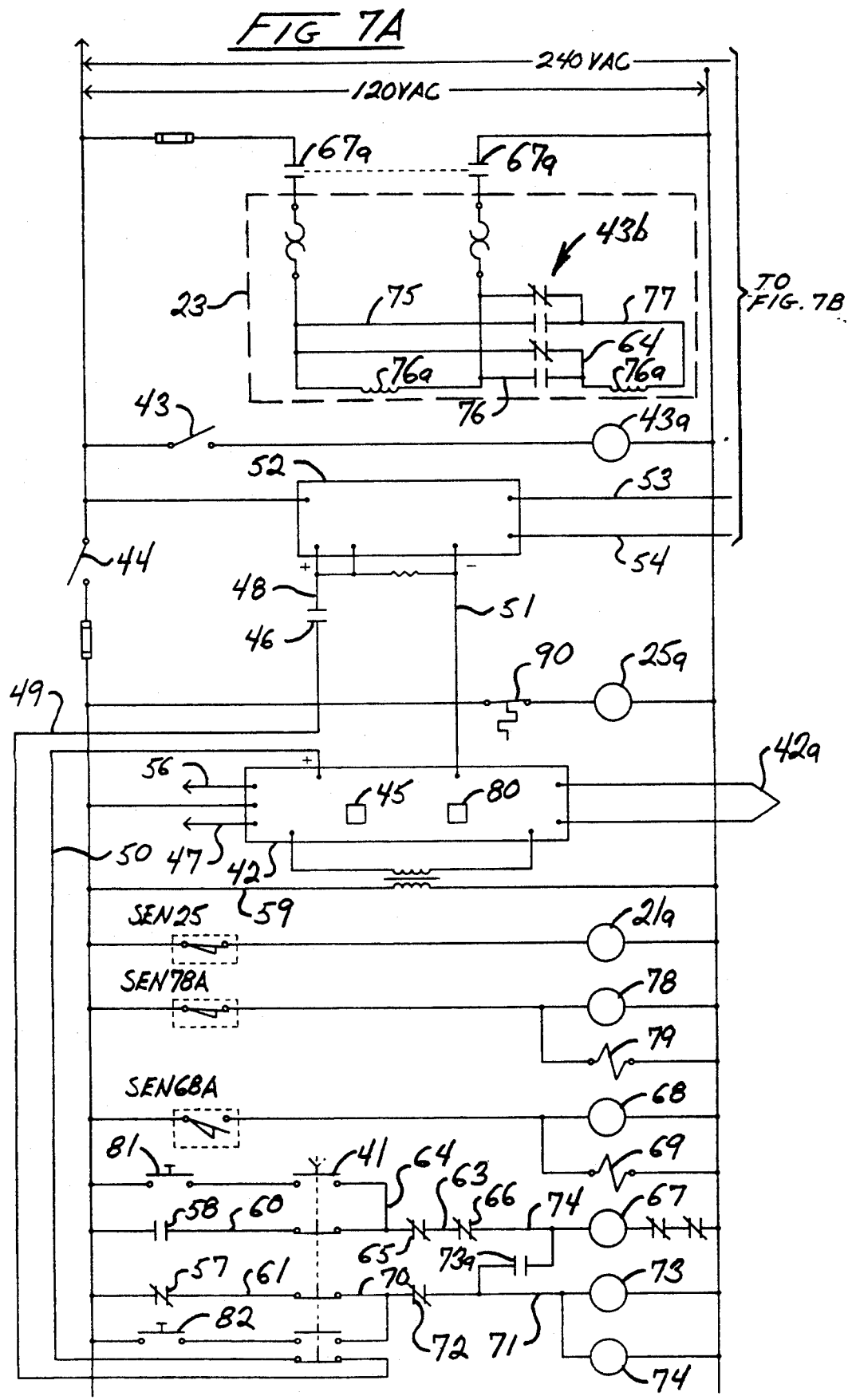
FIG. 7a is a wiring diagram of the control system for the temperature cycling test chambers.

With the test sample 21 facing the heat chamber 10 side, which position is assured by Sensor 25 thus permitting contact 46 to be activated sending current through wires 48 and 49, 50 and 51 allowing the ramp and soak temperature controller 42 to activate the power controller 52. Referring to FIG. 7b, the quartz tube heaters 18 raise the temperature of the sample at a rate of 50° F. per minute to 180° F. via the ramp and soak temperature controller 42 and the commercially available power controller 52 through wires 53, 53a, 54, 54a, and contacts 55. The temperature is maintained on the sample for five minutes, which is the soak period at 180° F. At the end of five minutes the wires 47 and 56 activate the ramp and soak temperature control switch so that contacts 57 open and contacts 58 close. Power flows through wires 59, contact 58, wires 60, 62, contact 65, wire 1 and contacts 66 to engage rotating wall section motor starter 67, revolving rotating test wall section 20 from the hot chamber side 10 to the cold chamber side 11.

As the wall section 20 gets to a position 20° before completely closing on the cold chamber 11 side, sensor 68a is activated energizing relay 68, and right hand hinged stop 32 solenoid valve 69. Relay 68 opens contact 65 removing power from wire 63, de-energizing relay 67 opening contacts 67a shutting off rotating test door motor 23. Right hand hinged stop solenoid valve 69 activates air cylinder 31, causing rotating right hand hinged stop 32 to come into position stopping wall section 20 in the precise closed position on the cold chamber 11 side.

The sample 21 is now in the cold chamber 11 side and is cooled to 0° F. at whatever rate occurs. When 0° F. is reached, the ramp and soak temperature control 42 holds the sample 21 in the cold chamber 11 for an additional ten minutes through its internal timer.

At completion of the ten minute period, the ramp and soak temperature controller contacts 58 open and contacts 57 close. See wires 59, 60, and 61. This causes power to flow through wires 59, 61, 70 and 71, contacts 57 and 72, to power timing relay 73 and reversing relay 74. Reversing relay 74 causes start winding on test wall section gear head motor 23 to be reversed. See wires 75, 76, 64, and 77. Adjacent to wire 76 are start winding 76a and run winding 76b, common to single phase electrical motors.

When timing relay 73 is energized by controller 42, the closing of contacts 73a is delayed for 1 second to allow relay 74 to complete it's reversing function as stated above, actuating rotating test wall section motor starter 67, revolving test wall section 20 from cold chamber 11 side to heat chamber 10 side. As test wall section 20 gets to a position 20° before completely closing on the heat chamber 11 side, sensor 78a is activated energizing relay 78 and left hand hinged stop solenoid valve 79. Relay 78 opens contacts 72 and deenergizes motor starter 67 through wires 70 and 71 to shut off rotating test wall section motor 23. Left hand hinged stop solenoid valve 79 activates an air cylinder similar to air cylinder 31, causing rotating left hand hinged stop similar to hinged stop 32, to come into position stopping wall section 20 in precise closed position at heat chamber 10 side.

This heat/cold cycle continues to operate until a failure of the test sample is noted and test is stopped by pushing stop button 80 on ramp and soak temperature controller 42. The test wall section 20 can be manually operated from the heat chamber to the cold chamber by switching auto/manual switch 41 to manual position and operating push button 81 and push button 82. If a malfunction would occur in ramp and soak temperature controller 42 or power control 52 that would allow the temperature in the heat chamber to rise to over 200° F., a high temperature alarm cutout 90, set at 200° F. along with relay 25a, which de-energizes the quartz heaters 18—18 by opening contacts 55, (manually reset) is incorporated to shut down power to quartz heaters 18—18 through wires 53, 53a, 54, 54a, and contacts 55.

Referring now more particularly to FIG. 7b, there is shown the electrical connections from the power controller and from line to the quartz heaters 18 in the hot chamber 10.

Thus it will be seen that a test sample when mounted on the rotating wall section 20 is connected to the appropriate sensing wires with conductive paint that the number of cycles per day can be rapidly increased between the hot chamber and the cold chamber in applicant's invention with adequate safeguards to protect the unit from overheating and from false readings.

While this invention has been described in its preferred embodiment, it is to be appreciated that variations therefrom may be made without departing from the true scope and spirit of the invention.

What is claimed:

1. A temperature cycling test device for exposing materials to repeated thermal cycles comprising:
a first zone maintained at a selected temperature, a second zone maintained at a different selected temperature from the temperature selected in said first zone, said first and second zones being adjacent each other and separated from each other by an insulated wall, said first and second zones also being insulated from the ambient air environment, said insulated wall having a rotatable portion therein, means for rotating said rotatable portion of said insulated wall on an axis substantially in the plane of said wall so as to alternately expose one side of said rotatable portion of said wall to said first zone and then to expose said one side of said rotatable portion of said wall to said second zone, and means for securing a test specimen of a material to said one side of said rotatable portion of said wall.

2. The temperature cycling test device of claim 1 which includes means for recording information concerning the condition of said test specimen.

3. The temperature cycling test device of claim 2 wherein conductive paint is applied to said test specimen and electric leads from said conductive paint are connected to a recording device.

4. The temperature cycling test device of claim 2 wherein the temperature of the test specimen is measured and recorded.

5. The temperature cycling test device of claim 1 wherein said first zone is cooled below ambient temperature and said second zone is heated above ambient temperature.

6. The temperature cycling test device of claim 1 wherein safety means is incorporated so as to make the device inoperative if the said rotatable portion of said insulated wall is not in the same plane as said wall.

7. The temperature cycling test device of claim 1 wherein said rotatable portion of said insulated wall is insulated from the rest of said wall.

8. The temperature cycling test device of claim 1 which includes means for controlling the dwell time that said rotatable portion of said wall is exposed to a first zone or to a second zone.

9. The temperature cycling test device of claim 1 wherein said second zone is movable away from said first zone and said insulated wall.

10. The temperature cycling test device of claim 9 wherein the zone which is movable is heated above ambient temperature.

* * * * *

UNITED STATES PATENT AND TRADEMARK OFFICE
CERTIFICATE OF CORRECTION

PATENT NO. : 5,147,136
DATED : September 15, 1992
INVENTOR(S) : Jeffrey W. Hartley, et.a l.

It is certified that error appears in the above-indentified patent and that said Letters Patent is hereby corrected as shown below:

On the Title page, item [75], inventor named Burch E. Zelner should read-- Burch E. Zehner--.

Column 3, line 54, wire 1 should be corrected to read wire 63--.

Signed and Sealed this

Seventh Day of September, 1993

Attest:

BRUCE LEHMAN

*Attesting Officer*  *Commissioner of Patents and Trademarks*